(12) United States Patent
Kim et al.

(10) Patent No.: US 12,383,146 B2
(45) Date of Patent: Aug. 12, 2025

(54) DIABETIC COMPLICATION MONITORING DEVICE AND DIABETIC COMPLICATION MANAGEMENT SYSTEM USING SAME

(71) Applicant: KOREA UNIVERSITY RESEARCH AND BUSINESS FOUNDATION, Seoul (KR)

(72) Inventors: Nan Hee Kim, Seoul (KR); Jaeyoung Kim, Seoul (KR); Da Young Lee, Gwacheon-si (KR); Ki Sun Lee, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 445 days.

(21) Appl. No.: 17/923,606

(22) PCT Filed: May 6, 2021

(86) PCT No.: PCT/KR2021/005639
§ 371 (c)(1),
(2) Date: Nov. 7, 2022

(87) PCT Pub. No.: WO2021/225370
PCT Pub. Date: Nov. 11, 2021

(65) Prior Publication Data
US 2023/0181046 A1    Jun. 15, 2023

(30) Foreign Application Priority Data

May 6, 2020   (KR) ........................ 10-2020-0053761

(51) Int. Cl.
*A61B 5/01*   (2006.01)
*A61B 5/00*   (2006.01)
(Continued)

(52) U.S. Cl.
CPC ............ *A61B 5/015* (2013.01); *A61B 5/0075* (2013.01); *A61B 5/1036* (2013.01);
(Continued)

(58) Field of Classification Search
CPC ..... A61B 5/015; A61B 5/0075; A61B 5/1036; A61B 5/7275; A61B 5/7405; A61B 5/742;
(Continued)

(56) References Cited

U.S. PATENT DOCUMENTS

2013/0296708 A1   11/2013  Zuzak et al.
2015/0057562 A1   2/2015   Linders et al.
(Continued)

FOREIGN PATENT DOCUMENTS

JP       6297696 B2       3/2018
JP     2019-519294 A      7/2019
(Continued)

OTHER PUBLICATIONS

PCT/KR2021/005639 english translation Sep. 1, 2021.*
International Search Report for PCT/KR2021/005639 mailed Sep. 1, 2021 from Korean Intellectual Property Office.

*Primary Examiner* — Mark W. Bockelman
(74) *Attorney, Agent, or Firm* — Revolution IP, PLLC

(57) ABSTRACT

A diabetic complications monitoring apparatus and a diabetic complications monitoring system using the same, includes a support fixture having a liquid crystal color changing sheet that is located on an upper surface of the support fixture and displays a foot heat distribution based on a color, a transparent glass that is located on an upper surface of the liquid crystal color changing sheet and comes into contact with user's feet to support the user's feet, a foot heat distribution measurement unit that includes a camera for imaging the liquid crystal color changing sheet and extracts (Continued)

and outputs a foot heat distribution from an image of the camera, a processor that acquires and outputs whether a disease occurs, or a position and size of occurrence of a disease, based on the foot heat distribution, and a data input/output device that audioizes and visualizes an output result of the processor.

5 Claims, 3 Drawing Sheets

(51) Int. Cl.
    *A61B 5/103*     (2006.01)
    *G01G 19/44*     (2006.01)

(52) U.S. Cl.
    CPC .......... *A61B 5/7275* (2013.01); *G01G 19/44* (2013.01); *A61B 5/7405* (2013.01); *A61B 5/742* (2013.01); *A61B 2562/0247* (2013.01)

(58) Field of Classification Search
    CPC .......... A61B 2562/0247; A61B 5/0077; A61B 5/441; A61B 5/1032; A61B 5/4842; A61B 5/6829; A61B 5/7267; A61B 5/7425; A61B 5/447; A61B 5/746; A61B 5/7465; G01G 19/44; G01G 19/50; G16H 30/40; G16H 50/20; G16H 50/30
    See application file for complete search history.

(56) References Cited

U.S. PATENT DOCUMENTS

| | | | |
|---|---|---|---|
| 2017/0319115 A1* | 11/2017 | Cuccia | ............... A61B 5/14551 |
| 2018/0028079 A1 | 2/2018 | Gurevich et al. | |
| 2019/0200917 A1 | 7/2019 | Murphy et al. | |
| 2019/0209076 A1* | 7/2019 | Murphy | ............... A61B 5/7235 |
| 2020/0107732 A1 | 4/2020 | Cuccia et al. | |

FOREIGN PATENT DOCUMENTS

| | | |
|---|---|---|
| JP | 2019-527073 A | 9/2019 |
| KR | 10-2018-0071837 A | 6/2018 |
| KR | 10-1949840 B1 | 2/2019 |
| KR | 10-2019-0133026 A | 11/2019 |

* cited by examiner

DIABETIC COMPLICATION MONITORING DEVICE AND DIABETIC COMPLICATION MANAGEMENT SYSTEM USING SAME

TECHNICAL FIELD

The present invention relates to a diabetic complications monitoring apparatus which may more simply and effectively identify and notify diabetic complications, such as diabetic foot disease, and a diabetic complications management system using the diabetic complications monitoring apparatus.

BACKGROUND

Recently, the number of adult diseases has increased due to the improved living environment, and most of all, the number of patients with adult diseases such as diabetes is gradually increasing.

Chronic disease patients also need to visit a hospital but have to check blood sugar levels regularly and follow up conditions from time to time and take appropriate measures.

When the diabetic foot disease is not treated early, a leg may have to be amputated, and thus, it is important to perform early diagnosis. This is caused by a combination of an atherosclerotic vascular change and a diabetic neuropathy. In other words, when a small wound occurs in the foot, a blood flow is not smooth due to arteriosclerosis, and pain my not be felt due to neuropathy, and thus, the wound worsens to eventually develop into a foot ulcer.

According to the various pathophysiology, the temperature of diabetic foot is low in a place where there is occlusive vascular disorder and is high in a place where there is inflammation due to a small wound. Therefore, this change has to be detected early, and appropriate treatment has to be made, but it is very difficult to be examined for a foot in a diabetes clinic.

A current approach to prevention of the diabetic foot ulcers is patient education, foot skin and toenail care, proper footwear selection, and preventive hygiene.

Therefore, when patients themselves regularly monitor and pre-detect diabetic foot disease, amputation of a leg may be reduced by preventing ulcers and surgical procedures through more active hygiene and therapeutic interventions.

Korean patent application No. 10-2018-0071837 and so on propose a system for measuring the temperature of a user's foot to prevent foot disease of a diabetic patient. However, there is disadvantages in that a thermal imaging system is expensive and a temperature sensor may measure only a narrow area causing not to measure the entire foot. In addition, there is a limitation in that an analysis algorithm using foot heat data of a diabetic patient is not used.

SUMMARY OF INVENTION

Technical Problem

Therefore, the present invention provides a diabetic complications monitoring apparatus that may more simply and effectively identify and notify diabetic complications such as a diabetic foot disease by measuring and analyzing a foot heat distribution based on images, and a diabetic complications management system including the diabetic complications monitoring apparatus.

In addition, a diabetic complication monitoring apparatus that may predict disease information, such as diabetic complications and blood sugar, by additionally using at least one of a foot pressure distribution, a weight change pattern, a Raman spectrum, and a near-infrared spectrum, and particularly, by using an artificial intelligence network method, and a diabetic complications management system.

Solution to Problem

According to an embodiment of the present invention, in order to solve the technical problem, a diabetic complications monitoring apparatus includes a support fixture having a plate shape, a liquid crystal color changing sheet that is located on an upper surface of the support fixture and displays a foot heat distribution based on a color, a transparent glass that is located on an upper surface of the liquid crystal color changing sheet and comes into contact with user's feet to support the user's feet, a foot heat distribution measurement unit that includes a camera for imaging the liquid crystal color changing sheet and extracts and outputs a foot heat distribution from an image of the camera, a processor that acquires and outputs whether a disease occurs, or a position and size of occurrence of a disease, based on the foot heat distribution, and a data input/output device that audioizes and visualizes an output result of the processor to guide a user or notify a preset external device.

It is characterized in that the diabetic complications monitoring apparatus further includes a foot pressure distribution measurement unit which measures a foot pressure distribution by using a pressure sensor array between the liquid crystal color changing sheet and the support fixture or between the transparent glass and the liquid crystal color changing sheet.

It is characterized in that the diabetic complications monitoring apparatus further includes a light spectrum measurement unit which is attached to a side surface of the transparent glass and measures at least one of a Raman spectrum and a near-infrared spectrum for a user's skin.

It is characterized in that a weight change measurement unit that measures and collects a user's weight by using a weight measurement sensor attached to a lower portion of one of the liquid crystal color changing sheet and the support fixture and acquires and outputs a weight change pattern.

It is characterized in that the processor includes a disease prediction model obtained by previously learning a correlation between the measurement information and disease information and further includes a function of predicting diabetic complications corresponding to at least one of a foot heat distribution, a foot pressure distribution, a weight change pattern, a Raman spectrum, and a near-infrared spectrum through the disease prediction model, the measurement information includes at least one of the foot heat distribution, the foot pressure distribution, the weight change pattern, the Raman spectrum, and the near-infrared spectrum, and the disease information includes at least one of the diabetic complications and blood sugar.

According to another embodiment of the present invention, in order to solve the technical problem, a diabetic complications management system includes a patient monitoring apparatus that measures at least one of a foot heat distribution, a foot pressure distribution, a weight change pattern, a Raman spectrum, and a near-infrared spectrum of each patient and generates and outputs measurement information, a patient information management device that acquires disease information of each patient and maps and stores the measurement information, and disease prediction server that generates a plurality of learning data in which a correlation between measurement information and disease information is defined based on information stored in the patient information management device, trains repetitively a disease prediction model, and acquires the disease information corresponding to new measurement information through the disease prediction model and provides the disease information when the patient monitoring apparatus transmits the new measurement information.

It is characterized in that the patient monitoring apparatus includes a support fixture having a plate shape, a liquid crystal color changing sheet that is located on an upper surface of the support fixture and displays a foot heat distribution based on a color, a transparent glass that is located on an upper surface of the liquid crystal color changing sheet and comes into contact with user's feet to support the user's feet, a foot heat distribution measurement unit that includes a camera for imaging the liquid crystal color changing sheet and extracts and outputs a foot heat distribution from an image of the camera, a foot pressure distribution measurement unit that measures a foot pressure distribution by using a pressure sensor array between the liquid crystal color changing sheet and the support fixture or between the transparent glass and the liquid crystal color changing sheet, a light spectrum measurement unit that is attached to a side surface of the transparent glass and measures at least one of a Raman spectrum and a near-infrared spectrum for a user's skin, a weight change measurement unit that measures and collects a user's weight by using a weight measurement sensor attached to a lower portion of one of the liquid crystal color changing sheet and the support fixture and acquires and outputs a weight change pattern, and a processor that generates and outputs measurement information including at least one of the foot heat distribution, the foot pressure distribution, the weight change pattern, the Raman spectrum, and the near-infrared spectrum, or receives the disease information to audioize and visualize the disease information and outputs the audioized and visualized disease information.

Advantageous Effects

In the present invention, diabetic complications such as a diabetic foot disease may be identified and notified more simply and effectively by measuring and analyzing a foot heat distribution based on an image obtained by using a liquid crystal color changing sheet and a camera.

In addition, at least one of a foot pressure distribution, a weight change pattern, a Raman spectrum, and a near-infrared spectrum is additionally acquired and used, and particularly, disease information, such as diabetic complications and blood sugar, may be predicted by using an artificial intelligence network method, and thus, more reliable disease diagnosis information may be acquired and provided more quickly and accurately.

BEST MODE FOR INVENTION

Figure 1:
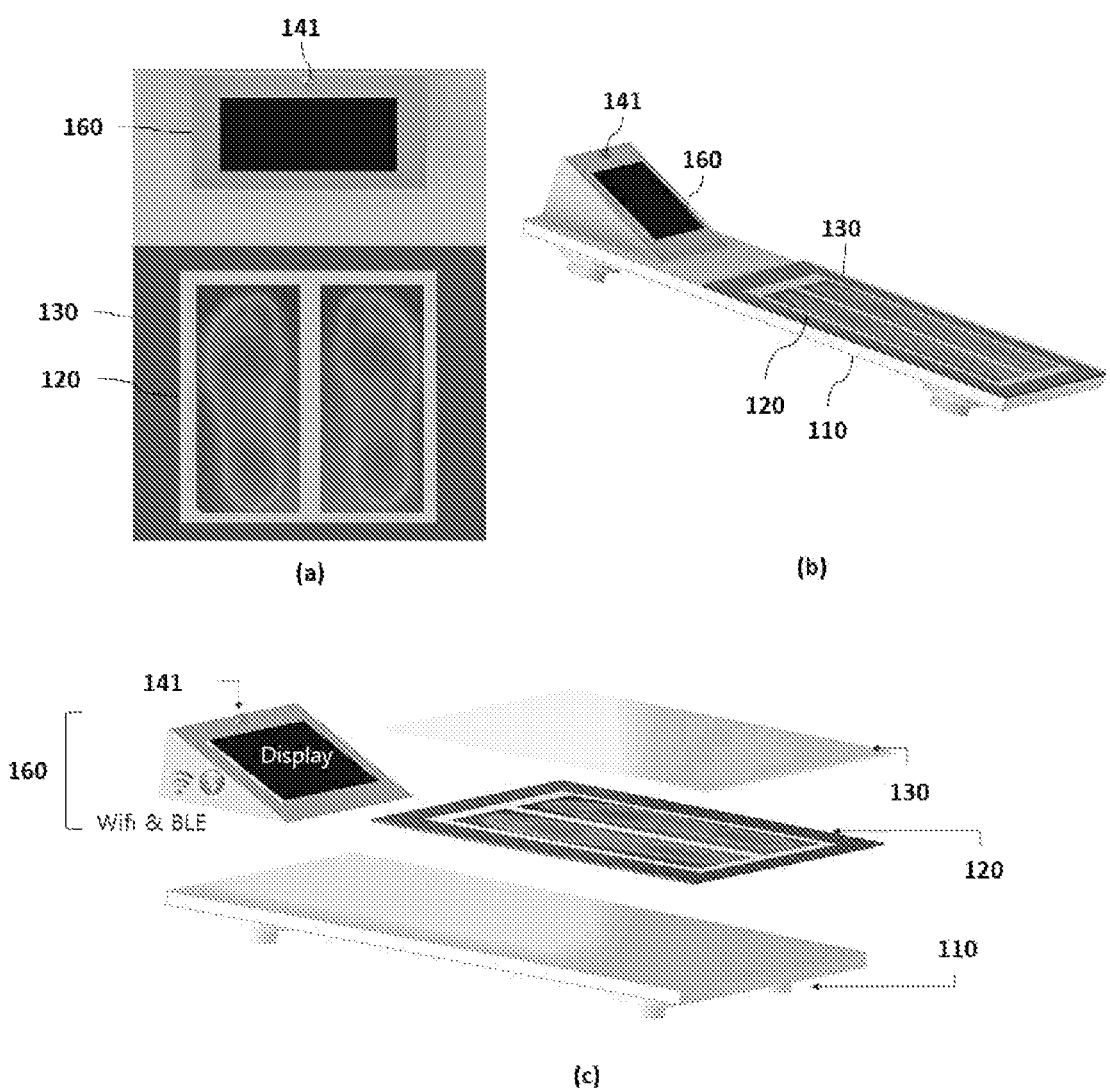
FIGS. 1 and 2 illustrate a diabetic complications monitoring apparatus according to a first embodiment of the present invention.

Hereinafter, the present invention will be described in detail with reference to the accompanying drawings.

However, in describing the present invention, when it is determined that a detailed description of a related well-known function or configuration may unnecessarily obscure the gist of the present invention, the detailed description thereof is omitted. Even in a case in which terms are the same, when the indicated parts are different from each other, the reference numerals do not match each other.

The terms to be described below are set in consideration of functions of the present invention, which may change depending on intentions or customs of medical personnel, such as experimenters or measurers, so definitions thereof should be made based on content throughout the present specification.

In the present specification, terms such as first and second may be used to describe various components, but the components are not limited by the terms. The terms are used only for the purpose of distinguishing one component from another. For example, the first component may be referred to as the second component, and similarly, the second component may also be referred to as the first component without departing from the scope of the present invention. "and/or" includes a combination of a plurality of related listed items or any one thereof.

The terms used herein are used only to describe specific embodiments and are not intended to limit the present invention. A singular expression includes a plural expression unless stated otherwise.

Unless defined otherwise, all terms, which re used herein and include technical or scientific terms, have the same meaning as commonly understood by those skilled in the art to which the present invention belongs. Terms defined in a commonly used dictionary should be interpreted as having a meaning consistent with the meaning in the context of the related art, and should not be interpreted in an ideal or excessively formal meaning unless explicitly defined in the present application.

Hereinafter, the present invention will be described in detail with reference to the accompanying drawings. In describing the present invention, the same reference numerals are used for the same components in the drawings and redundant descriptions of the same components are omitted to facilitate the overall understanding.

Figure 2:
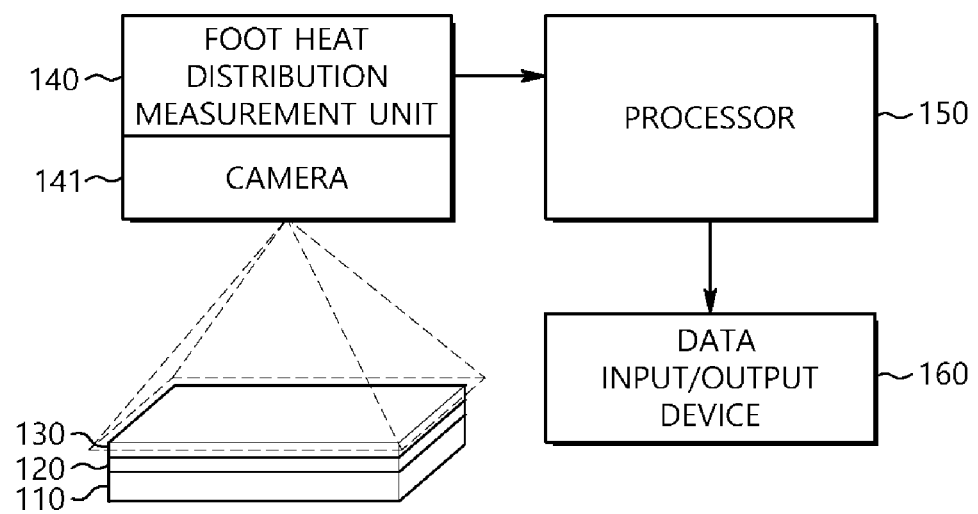

FIGS. 1 and 2 illustrate a diabetic complications monitoring apparats according to a first embodiment of the present invention, in which (a) of FIG. 1 is a front view, (b) of FIG. 1 is a side view, and (c) of FIG. 1 is an exploded view, and FIG. 2 is a detailed configuration diagram.

Referring to FIGS. 1 and 2, a monitoring apparatus 100 of the present invention includes a support fixture 110 having a plate shape, a liquid crystal color changing sheet 120 that is located on an upper surface of the support fixture 110 and displays a foot heat distribution based on a color, a transparent glass 130 that is located on an upper surface of the liquid crystal color changing sheet 120 and comes into contact with user's feet to support the user's feet, a foot heat distribution measurement unit 140 that includes a camera 141 for imaging the liquid crystal color changing sheet 120 and extracts and outputs a foot heat distribution from an image of the camera 141, a processor 150 that acquires and outputs whether a disease occurs, or a position and size of occurrence of a disease, based on the foot heat distribution, a data input/output device 160 that audioizes and visualizes an output result of the processor 150 to guide a user or notify a preset external device, and so on.

The liquid crystal color changing sheet 120 is a material having characteristics that a color changes according to the temperature of a contact object and immediately displays a color distribution that matches 1:1 with a foot heat distribution of a user when the user's feet are placed on the liquid crystal color changing sheet 120.

Accordingly, in the present invention, when a user is on the liquid crystal color changing sheet 120, the liquid crystal color changing sheet 120 displays a color distribution corresponding to the user's foot heat distribution. In addition, when the user comes down from the liquid crystal color changing sheet 120, the foot heat distribution is obtained based on an image obtained by imaging the liquid crystal color changing sheet 120 through the camera 141.

The processor 150 compares the foot heat distribution obtained by the foot heat distribution measurement unit 140 with a preset reference value and analyzes the comparison result, and checks and notifies that diabetic complications occur when a region having an abnormal temperature value is detected. In addition, the processor 150 may identify and notify a position and a size of the diabetic complications based on relative position and size of the region having the abnormal temperature value.

The data input/output device 160 of the present invention may include a small monitor, a small speaker, a short-range wireless communication module, a control panel, and so on, and audioizes and visualizes output data of the processor 150 through the small monitor and the small speaker to perform a user guide operation, and transmits in real time the output data of the processor 150 to a preset external device through the short-range wireless communication module. The data input/output device 160 acquires various control values manually input by a user through the control panel and transmits the various control values to the processor 150.

In addition, it is preferable that the camera 141 is implemented integrally with the support fixture 110, but, when necessary, the communication module may be configured as a communicable and detachable type.

However, when the camera 141 is configured as an integrated support fixture, a protrusion portion 111 may be additionally formed on one side of the support fixture 110, and the camera 141 may be provided on the protrusion portion 111. This is to image all of the foot heat distributions displayed on the liquid crystal color changing sheet 120 by allowing an image capturing range of the camera 141 to cover the entire area of the liquid crystal color changing sheet.

Figure 5:
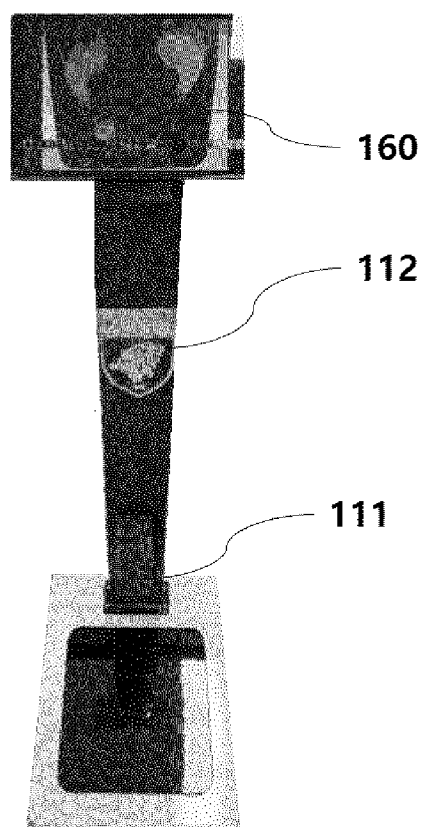
FIG. 5 is a view illustrating an embodiment of a diabetic complications monitoring apparatus according to the present invention.

FIG. 5 is a view illustrating an embodiment of the diabetic complications monitoring apparatus according to the present invention. As illustrated in FIG. 5, the data input/output device 160 may also be installed on an additional support fixture 112 formed to extend toward an upper portion of the support fixture for the sake of a user when the user checks an output result, and in this case, the protrusion portion 111 may be formed on a lower portion of the additional support fixture 112.

Figure 3:
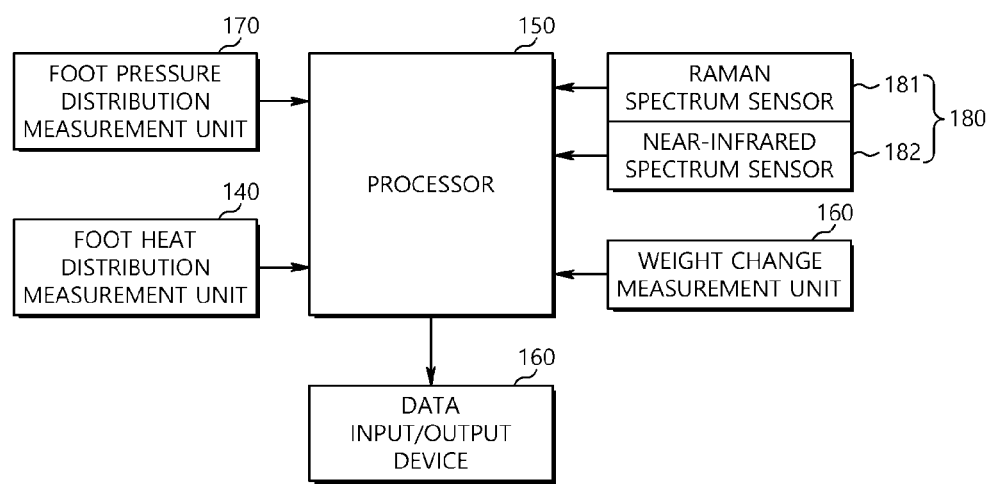
FIG. 3 is a diagram illustrating a diabetic complications monitoring apparatus according to a second embodiment of the present invention.

FIG. 3 is a diagram illustrating a diabetic complications monitoring apparatus according to a second embodiment of the present invention.

Referring to FIG. 3, the monitoring apparatus 100 of the present invention may further include at least one of a foot pressure distribution measurement unit 170, a light spectrum measurement unit 180, and a weight change measurement unit 190 in addition to the support fixture 110, the liquid crystal color changing sheet 120, the transparent glass 130, the camera 141, the processor 150, and the data input/output device 160.

The foot pressure distribution measurement unit 170 includes a pressure sensor array between the liquid crystal color changing sheet 120 and the support fixture 110 or between the transparent glass 130 and the liquid crystal color changing sheet 120 to measure a pressure distribution of feet of a user and notifies the user of the measurement result.

The light spectrum measurement unit 180 may include at least one of a Raman spectrum sensor 181 and a near-infrared spectrum sensor 182 attached to a side surface of the transparent glass 130.

Both the Raman spectrum sensor 181 and the near-infrared spectrum sensor 182 may each be configured with a light source that emits light to a user's skin, and a spectrometer that detects absorbed, scattered, or reflected light of the user's skin to measure light spectrum data, and use the transparent glass 130 as a light transmission path.

In this case, the light source may be configured with a light emitting diode (LED), a laser diode, or so on, and a wavelength and a frequency of the light changes depending on the type of sensor. The spectrometer may be configured with a photo diode, a photo transistor (PTr), a charge-coupled device (CCD), or so on.

The weight change measurement unit 190 includes a weight measurement sensor attached to a lower portion of the liquid crystal color changing sheet 120 or the support fixture 110 to track and monitor a user's weight measured by the weight measurement sensor in a period of time and acquires and outputs a user's weight change pattern.

In this case, the processor 150 of the present invention includes a disease prediction model obtained by previously learning a correlation between measurement information (that is, at least one of a foot heat distribution, a foot pressure distribution, a Raman spectrum, a near-infrared spectrum, and a weight change pattern) and disease information (that is, at least one of diabetic complications and blood sugar).

In addition, when new measurement information is acquired by a user, diabetic complications corresponding to the newly acquired measurement information through the disease prediction model is predicted, and the prediction result is notified to at least one of the user and an external device.

In this case, the disease prediction model may be built and trained based on a machine learning algorithm, and the machine learning algorithm may include a partial least squares regression, a linear regression, a neural network, a decision tree, a genetic algorithm, genetic programming, k-nearest neighbor, a radial basis function network, a random forest, a support vector machine, deep learning, and so on but is not limited thereto.

As described above, the diabetic complications monitoring apparatus of the present invention acquires and utilizes a foot heat distribution by using a liquid crystal color changing sheet to simply check whether a user has diabetic complications.

In addition, various types of information, such as a foot pressure distribution, a Raman spectrum, a near-infrared spectrum, and a weight change pattern may be additionally used, and thus, occurrence of diabetic complications may be more accurately diagnosed.

Figure 4:
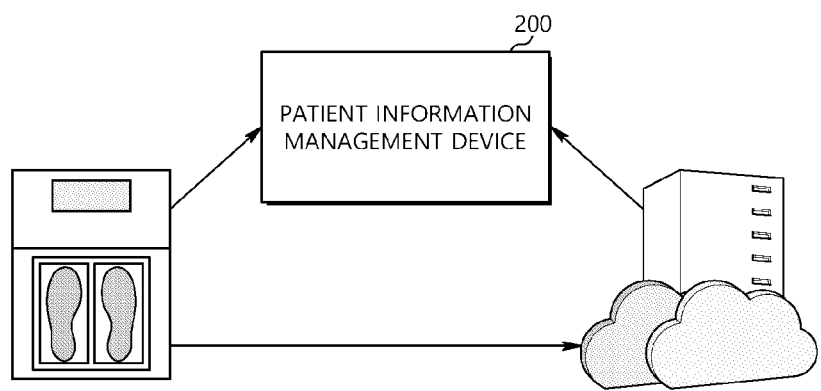
FIG. 4 is a view illustrating a diabetic complications management system using a diabetic complications monitoring apparatus, according to the present invention.

FIG. 4 is a view illustrating a diabetic complications management system using a diabetic complications monitoring apparatus, according to the present invention.

Referring to FIG. 4, the diabetic complications management system of the present invention includes a patient information management device 200, and a disease prediction server 300 in addition to the patient monitoring apparatus 100 described above.

The patient monitoring apparatus 100 measures at least one of a foot heat distribution, a foot pressure distribution, a Raman spectrum, and a near-infrared spectrum of each patient and generates and outputs measurement information.

The patient information management device 200 may be configured with a patient terminal or a medical staff terminal that may be interconnected to the patient monitoring apparatus 100 in a short-range wireless communication manner to acquire disease information of each patient and then map and store the measurement information.

In this case, the disease information may be diabetes-related information, such as diabetic complications information and blood sugar information but is not limited thereto.

The disease prediction server 300 may include a model learning unit, a prediction unit, and so on, and may be interconnected to the patient information management device 200 in a remote wireless communication manner.

The model learning unit generates a plurality of learning data in which a correlation between measurement information and disease information is defined based on information stored and managed by the patient information management device 200, and then repeatedly trains a disease prediction model through the plurality of learning data.

When the patient monitoring apparatus 100 requests a disease diagnosis while acquiring and transmitting new measurement information, the prediction unit acquires disease information corresponding to the new measurement information through the disease prediction model, and then provides the disease information to the patient monitoring apparatus 100 or a system manager.

The above description is merely illustrative of the technical idea of the present invention, and various modifications and changes may be made without departing from the essential characteristics of the present invention by those skilled in the art to which the present invention belongs. Therefore, the embodiments disclosed in the present invention are not intended to limit the technical idea of the present invention, but to describe, and the scope of the technical idea of the present invention is not limited by the embodiments. The protection scope of the present invention should be interpreted by the following claims, and all technical ideas within the scope equivalent thereto should be construed as being included in the scope of the present invention.

The invention claimed is:

1. A diabetic complications monitoring apparatus comprising:
   a support fixture having a plate shape;
   a liquid crystal color changing sheet that is located on an upper surface of the support fixture and displays a foot heat distribution based on a color;
   a transparent glass that is located on an upper surface of the liquid crystal color changing sheet and comes into contact with user's feet to support the user's feet;
   a foot heat distribution measurement unit that includes a camera for imaging the liquid crystal color changing sheet and extracts and outputs a foot heat distribution from an image of the camera;
   a processor that acquires and outputs whether a disease occurs, or a position and size of occurrence of a disease, based on the foot heat distribution;
   a data input/output device that audioizes and visualizes an output result of the processor to guide the user or notify a preset external device; and
   a light spectrum it at ed to a side surface of the transparent glass and configured to measure least one of a Raman and a near-infrared spectrum of the user's skin, wherein the light spectrum measurement unit comprises a light source that emits light through the transparent glass as a light transmission path toward the user's skin and a spectrometer that detects light absorbed, scattered, or reflected from the user's skin to obtain spectral data.

2. The diabetic complications monitoring apparatus of claim 1, further comprising
   a foot pressure distribution measurement unit that measures a foot pressure distribution of the user's feet using a pressure sensor array disposed between the liquid crystal color changing sheet and the support fixture, or between the transparent glass and the liquid crystal color changing sheet.

3. The diabetic complications monitoring apparatus of claim 1, further comprising:
   a weight change measurement unit that measures the user's weight using a weight measurement sensor attached to a lower portion of one of the liquid crystal color changing sheet and the support fixture and acquires and outputs a weight change pattern of the user.

4. The diabetic complications monitoring apparatus of claim 1, wherein
   the processor includes a disease prediction model obtained by previously learning a correlation between measurement information and disease information, and is configured to predict diabetic complications corresponding to at least one of a foot heat distribution, a foot pressure distribution, a weight change pattern, a Raman spectrum, and a near-infrared spectrum through the disease prediction model,
   the measurement information includes at least one of the foot heat distribution, the foot pressure distribution, the weight change pattern, the Raman spectrum, and the near-infrared spectrum, and the disease information includes at least one of the diabetic complications and blood sugar.

5. A diabetic complications monitoring system comprising:
   a patient monitoring apparatus that measures at least one of a foot heat distribution, a foot pressure distribution, a weight change pattern, a Raman spectrum, and a near-infrared spectrum of each patient and generates and outputs measurement information;
   a patient information management device that acquires disease information of each patient and maps and stores the measurement information; and
   a disease prediction server that generates a plurality of learning data in which a correlation between measurement information and disease information is defined based on information stored in the patient information management device, trains repetitively a disease prediction model, and acquires the disease information corresponding to new measurement information through the disease prediction model and provides the disease information when the patient monitoring apparatus transmits the new measurement information,
   wherein the patient monitoring apparatus includes:
   a support fixture having a plate shape;

a liquid crystal color changing sheet that is located on an upper surface of the support fixture and displays a foot heat distribution based on a color;

a transparent glass that is located on an upper surface of the liquid crystal color changing sheet and comes into contact with user's feet to support the user's feet;

a foot heat distribution measurement unit that includes for imaging the liquid crystal color changing sheet and extracts and outputs a foot heat distribution from an image of camera;

a foot pressure distribution measurement unit that measure distribution by using a pressure sensor array between the liquid crystal color charging sheet and the support fixture or between the transparent glass and the liquid crystal color changing sheet;

a light spectrum vent nit that is attached to a side surface of the transparent glass and measures at least one of a Re man spectrum and a near infrared spectrum for a user's skin;

a weight change measurement unit that measures and collects a user's weight by using a weight measurement sensor attached to a lower portion of one of the liquid crystal color changing sheet and the support fixture and acquires and outputs a weight change pattern, and a processor that generates and outputs is measurement information including at least one of the foot heat distribution, the foot pressure distribution, the weight change pattern, the Raman spectrum, and the near-infrared spectrum, receives the disease information to audioize and visualize the disease information and outputs the audioized and visualized disease information, wherein the light spectrum measurement unit is attached to a side surface of the transparent glass and configured to measure at least one of aspect a near-infrared spectrum of the user's skin, wherein the light spectrum measurement unit comprises a light source that emits light through the transparent glass as a light transmission path toward the user's skin and a spectrometer that detects light absorbed, scattered, or reflected from the user's skin to obtain spectral data.

* * * * *